United States Patent
Soga et al.

(10) Patent No.: US 7,224,460 B2
(45) Date of Patent: May 29, 2007

(54) MAPPING-MEASUREMENT APPARATUS (75) Inventors: Noriaki Soga, Hachioji (JP); Jun Koshoubu, Hachioji (JP); Hiroshi Tsukada, Hachioji (JP)

(73) Assignee: Jasco Corporation, Hachioji-shi, Tokyo (JP)

( * ) Notice: Subject to any disclaimer, the term of this patent is extended or adjusted under 35 U.S.C. 154(b) by 200 days.

(21) Appl. No.: 10/970,518

(22) Filed: Oct. 21, 2004

(65) Prior Publication Data
US 2005/0088656 A1 Apr. 28, 2005

(30) Foreign Application Priority Data
Oct. 24, 2003 (JP) ............... 2003-364804

(51) Int. Cl.
*G01N 21/00* (2006.01)
*G01N 21/55* (2006.01)

(52) U.S. Cl. .................... 356/444; 356/445
(58) Field of Classification Search ......... 356/444, 356/445
See application file for complete search history.

(56) References Cited

U.S. PATENT DOCUMENTS 3,180,217 A * 4/1965 Argyle et al. ............. 359/730
3,705,755 A * 12/1972 Baer ......................... 359/202
5,978,095 A * 11/1999 Tanaami .................... 356/445
6,633,384 B1 * 10/2003 Drake et al. ............... 356/432

FOREIGN PATENT DOCUMENTS

JP 04-110960 9/1992
JP 3329018 7/2002

OTHER PUBLICATIONS

English Translation of the Abstract of Japanese Publication No. 04-110960, published Sep. 25, 1992.
Shimadzu Corp.; title Infrared Microscope; English translation of the Abstract of Japanese Patent No. 3329018, issued Jul. 19, 2002; Publication No. 07-063994, published Mar. 10, 1995; Application No. 05-234025, filed Aug. 25, 1993.

\* cited by examiner

*Primary Examiner*—Layla G. Lauchman
*Assistant Examiner*—Jonathan Skovholt
(74) *Attorney, Agent, or Firm*—Rankin, Hill, Porter & Clark LLP (57) ABSTRACT

A mapping-measurement apparatus includes a light illumination unit, a photodetector for detecting, through an aperture, reflection light or transmission light from a sample, and adjustable scanning mirrors on the illumination and detection sides of the sample, each mirror having two independent rotational axes about which they can be independently rotated by a controller. The aperture restricts light incident on the photodetector from a predetermined portion of the sample surface.

6 Claims, 7 Drawing Sheets

OBSERVATION AREA

MAPPING-MEASUREMENT APPARATUS

RELATED APPLICATIONS

This application claims priority to the Japanese Patent Application No. 2003-364804 dated on Oct. 24, 2003 is hereby incorporated with reference for all purposes.

BACKGROUND OF THE INVENTION

1. Field of the Invention

The present invention relates to mapping-measurement apparatuses, and more particularly, to improvements of the mapping mechanisms thereof.

2. Prior Art

Various microscopes are used to check the molecular structures and so on of organic and other substances attached to a surface of a solid. In infrared microscopes, for example, a specific minute portion of a measurement surface of a sample held on a stage is illuminated with infrared rays, and a transmission, reflection, absorption or other type of spectrum is measured. To measure the specific minute portion of the sample in microscopes such as those described above, an aperture is provided in the optical path to remove light coming from portions other than the specific minute portion. In other words, only a portion for which measurement is to be performed is selected, and a photodetector receives light only from that portion to acquire data (for example, see Japanese Unexamined Utility Model Registration Application Publication No. 1992-110960).

In microscopes such as those described above, it is difficult to measure the entire sample to be measured at once because a high magnification is used. Therefore, mapping measurement is performed to measure the entire sample or a specific area of the sample in a uniform manner (for example, see Japanese Unexamined Patent Registration Application Publication No. 1995-63994).

In the configuration used in the mapping measurement, the sample is generally placed on a stage that can be driven, and the sample itself is moved to measure different portions.

Since very precise control is required for this stage driving, it is impossible to use manual movement in the mapping measurement. Therefore, electronically controlled automatic stages have been used.

However, one drawback of mapping measurement that employs an automatic stage is that the mapping-measurement apparatuses become complicated due to the stage driving section.

SUMMARY OF THE INVENTION

It is an object of the present invention is to provide a mapping-measurement apparatus having a simple structure.

A mapping-measurement apparatus of the present invention comprise: a light illumination unit for illuminating the sample with light; a photodetector for detecting, through an aperture, reflection light or transmission light coming from the sample; and a detection-side scanning mirror provided in the optical path from the sample to the aperture. The aperture restricts light to be detected by the photodetector only to light coming from a given measurement portion only on the surface of the sample. The detection-side scanning mirror is structured such that the direction of a reflection plane thereof can be changed. The direction of the reflection plane of the detection-side scanning mirror is changed with respect to the incident direction of the reflection light or the transmission light coming from the sample to change the measurement portion on the surface of the sample where measurement is performed by the photodetector, to apply mapping measurement to the predetermined area of the sample.

In the mapping-measurement apparatus according to the present invention, it is preferable that the mapping-measurement apparatus further comprise an illumination-side scanning mirror for directing the light emitted by the light illumination unit to the sample, wherein the illumination-side scanning mirror is structured such that the direction of a reflection plane thereof can be changed, and the direction of the reflection plane of the illumination-side scanning mirror is changed with respect to the incident direction of the light emitted by the light illumination unit to change an illumination portion on the surface of the sample.

In the mapping-measurement apparatus according to the present invention, it is preferable that the detection-side scanning mirror has two rotation axes independent from each other, and the mapping-measurement apparatus further comprise a controller for controlling the amounts of rotation on the rotation axes of the scanning mirror.

In the mapping-measurement apparatus according to the present invention, it is preferable that the illumination-side scanning mirror has two rotation axes independent from each other, and the mapping-measurement apparatus further comprising a controller for controlling the amounts of rotation on the rotation axes of the scanning mirror.

In the mapping-measurement apparatus according to the present invention, it is preferable that the mapping-measurement apparatus further comprise an objective mirror disposed in the optical path between the illumination-side scanning mirror and the sample, for focusing the light emitted by the light illumination unit on a specific minute portion on the surface of the sample.

In the mapping-measurement apparatus according to the present invention, it is preferable that the mapping-measurement apparatus further comprise an objective mirror disposed in the optical path between the sample and the detection-side scanning mirror, for collecting reflection light and/or transmission light coming from a specific minute portion on the surface of the sample.

In the mapping-measurement apparatus according to the present invention, it is preferable that the photodetector is a single-element detector.

In the mapping-measurement apparatus according to the present invention, it is preferable that the photodetector is a multi-element detector.

DESCRIPTION OF THE PREFERRED EMBODIMENT

Figure 1:
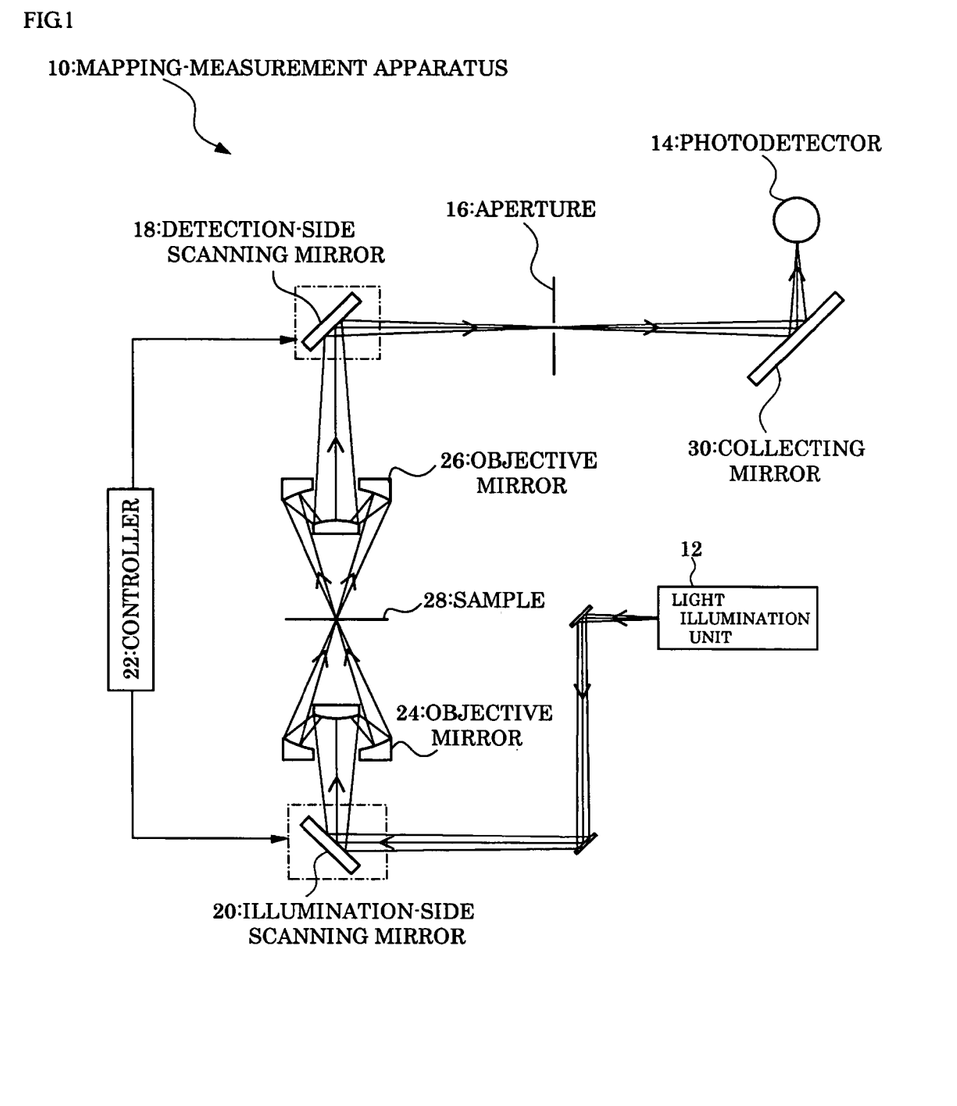
FIG. 1 is an outline structural view of a mapping-measurement apparatus according to an embodiment of the present invention.

Preferred embodiments of the present invention will be described below by referring to the drawings. FIG. 1 is an outline structural view of a mapping-measurement apparatus according to an embodiment of the present invention. FIG. 1 shows an optical path used to measure light transmitted through a sample 28. A mapping-measurement apparatus 10 of the present embodiment is provided with a light illumination unit 12 for illuminating the sample with light, a photodetector 14 for detecting light reflected from or light transmitted through the sample 28, an aperture 16 disposed before the photodetector 14, for passing only the light transmitted through a specific portion on a surface of the sample 28, and a detection-side scanning mirror 18 disposed in the optical path between the sample 28 and the aperture 16.

The detection-side scanning mirror 18 is configured such that the direction of its reflection plane can be changed. The direction of the reflection plane of the mirror 18 can be changed with respect to the incident direction of the transmission light. In other words, setting the direction of the reflection plane of the detection-side scanning mirror 18 determines from which position on the surface of the sample 28 comes light passing through the aperture 16.

It is assumed in the present embodiment that an infrared absorption spectrum is measured. In this case, the light illumination unit 12 includes an infrared light source and a Michelson interferometer. This structure is the same as that normally used in Fourier-transform infrared spectroscopy. A dispersive spectroscope may also be used.

The mapping-measurement apparatus 10 also includes an objective mirror 24 for focusing light emitted from the light illumination unit 12 onto a specific portion on the sample 28, and an objective mirror 26 for collecting light transmitted through the sample 28. The objective mirrors 24 and 26 are formed of Cassegrain mirrors or others.

As the photodetector 14, a detector normally used for infrared measurement, such as an MCT detector or an InSb detector, can be used.

The aperture 16 is configured such that its opening size and shape can be changed in order to adjust the portion for which measurement is to be performed. In other words, the aperture blocks light transmitted through the portions other than the measurement portion, and selectively passes light coming from the measurement portion only. The detection-side scanning mirror 18 determines which part of the transmission light coming from the sample 28 advances toward the opening of the aperture 16.

It is also preferable to provide an illumination-side scanning mirror 20 for guiding light coming from the light illumination unit 12 to the sample 28. The illumination-side scanning mirror 20 is also configured such that the direction of its reflection plane can be changed. The direction of the reflection plane can be changed with respect to light coming from the light illumination unit 12. As a result, the portion of the sample illuminated with measurement light can be changed as desired.

Figure 2:
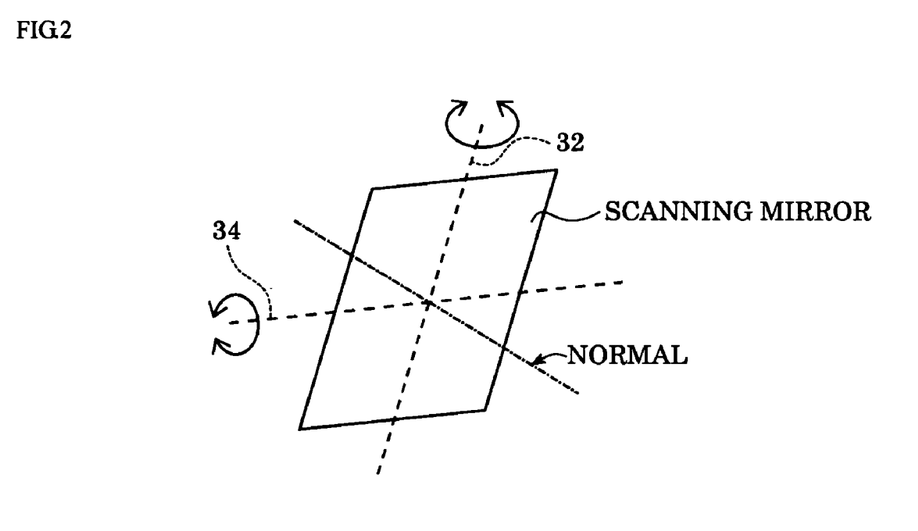
FIG. 2 is an explanatory drawing of a scanning-mirror.

The directions of the reflection planes of the detection-side and illumination-side scanning mirrors 18 and 20 are changed under the control of signals sent from a controller 22. To change the direction of the reflection plane of a mirror in a desired manner, the mirror needs to be made rotatable on two independent axes (not parallel to each other). As shown in FIG. 2, for example, a scanning mirror needs to be configured such that it can be rotated on rotation axes 32 and 34 perpendicular to each other and the direction of the mirror can be changed to any direction by controlling the amount of rotation with respect to each rotation axis. The control of the amounts of rotation is electronically performed by a stepper motor or the like such that the reflection plane is rotated and stopped at any specified angle. Since the direction of the normal of the reflection plane of the mirror can be precisely controlled, the reflection direction of light incident on the mirror is precisely controlled.

An outline structure of the present invention has been described so far. The operation thereof will be described next by referring to FIG. 1. Light emitted from the light illumination unit 12 is reflected by the illumination-side scanning mirror 20 toward the objective mirror 24. The light is emitted to a specific minute portion of the surface of the sample 28 by the objective mirror 24. The direction of the reflection plane of the illumination-side scanning mirror 20 is controlled by the controller 22 such that the illuminated portion matches the specific position on the surface of the sample 28. Light transmitted through the sample 28 is collected by the objective mirror 26 and directed toward the detection-side scanning mirror 18. The detection-side scanning mirror 18 reflects the transmission light coming from the sample 28 toward the aperture 16. The direction of the reflection plane of the detection-side scanning mirror 18 is adjusted such that light coming from the measurement portion advances toward the opening of the aperture 16. The aperture 16 blocks transmission light coming from the portions other than the measurement portion, and passes the light coming from the measurement portion only. Light passing through the aperture 16 is collected by a collecting mirror 30 and detected by the photodetector 14. Detected data is stored and processed by a data processing apparatus (not shown) formed of a computer and or the like. Since the aperture 16 limits the light received by photodetector, the minute portion of the sample can be measured precisely.

Figure 3:
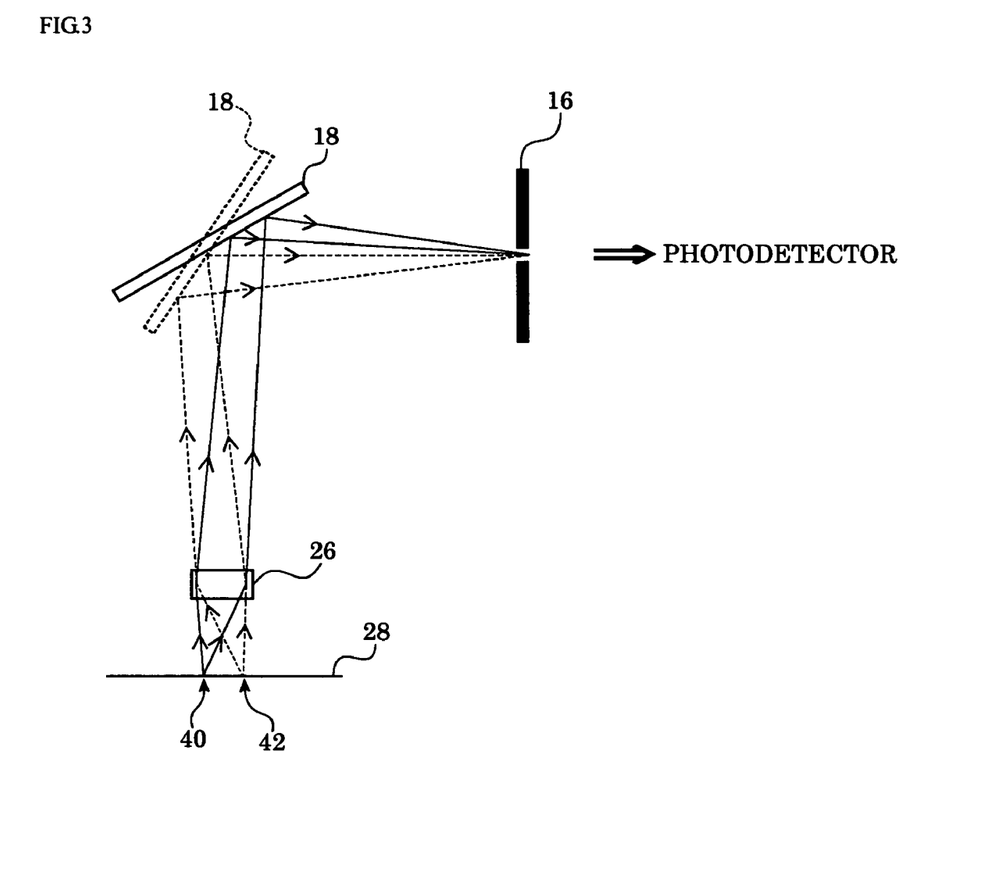
FIG. 3 is a view showing how the measurement portion of the sample is changed by the detection-side scanning mirror.

FIG. 3 is a view showing how the measurement portion of the sample 28 is changed by the detection-side scanning mirror 18. Solid lines indicate the direction of the mirror and the light beam obtained when the measurement portion is located at a position indicated by a reference numeral 40, and dotted lines indicate the direction of the mirror and the light beam obtained when the measurement portion is located at a position indicated by a reference numeral 42. Light coming from the surface of the sample 28 is collected by the objective mirror 26, and advances towards the detection-side scanning mirror 18. Light coming from the sample 28 advances in different directions depending on the position on the surface of the sample where the light is transmitted. Therefore, when the direction of the reflection plane of the mirror 18 is fixed, only the light coming from a particular portion on the surface of the sample corresponding to the direction of the reflection plane passes through the opening of the aperture 16, and light coming from the other portions is blocked. In other words, when the direction of the mirror is changed with respect to the light coming from the surface of the sample 28, light coming from a different measurement portion is sent to the opening of the aperture 16 among the light coming from the sample. Therefore, when the direction of the reflection plane of the mirror 18 is made variable, the measurement portion measured by the photodetector can be changed without moving the sample itself.

Figure 4:
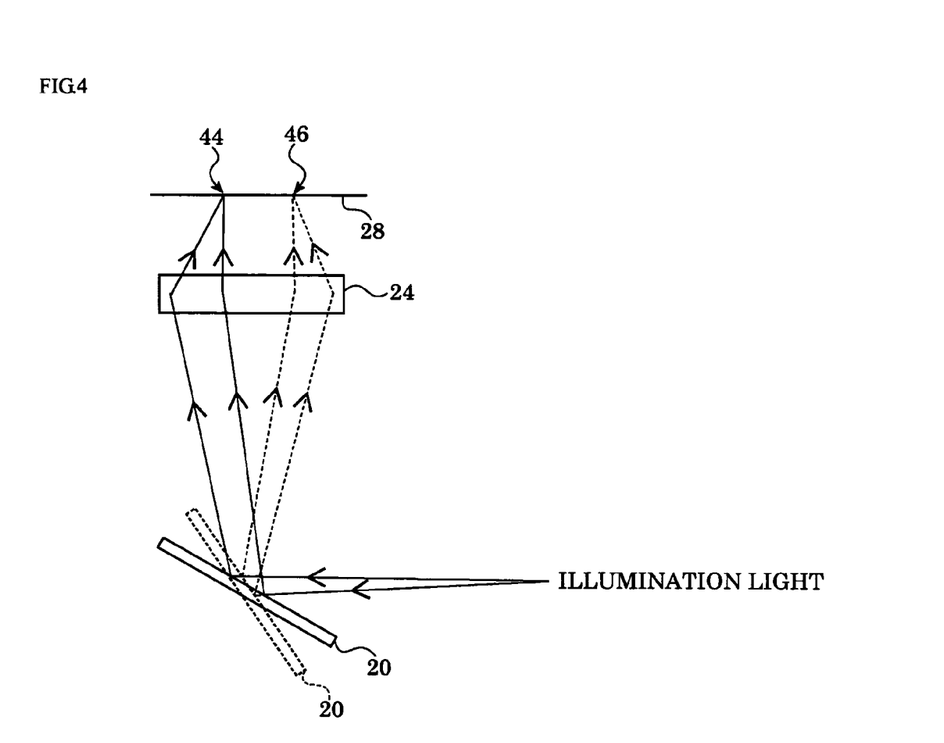
FIG. 4 is a view showing how the portion illuminated with light in the sample is changed by the illumination-side scanning mirror.

FIG. 4 is a view showing how the portion illuminated with light in the sample is changed by the illumination-side scanning mirror 20. In the same way as in FIG. 3, solid lines indicate the direction of the mirror and the light beam obtained when the illuminated portion is located at a position indicated by a reference numeral 44, and dotted lines indicate the direction of the mirror and the light beam obtained when the illuminated portion is located at a position indicated by a reference numeral 46. Illumination light is reflected by the illumination-side scanning mirror 20, collected by the objective mirror 24, and emitted to a specific portion on the surface of the sample 28. The propagating direction of light incident on the objective mirror 24 differs depending on the direction of the reflection plane of the mirror 20. As a result, the illuminated position on the surface of the sample 28 changes. Therefore, in the same way as in FIG. 3, the illuminated position on the sample can be easily changed by changing the direction of the mirror 20.

These scanning mirrors can be adjusted in advance by using, for example, a plate having an opening and made from a material which does not transmit infrared light. More specifically, in the apparatus shown in FIG. 1, the plate is disposed instead of the sample 28 such that the opening of the plate is located at a predetermined position. Infrared light is emitted to perform measurement as in usual measurement. The directions of the illumination-side 20 and detection-side scanning mirrors 18 are adjusted so as to obtain the maximum detection signal at the photodetector 14. The direction of each scanning mirror is stored in a data processing apparatus such as a computer as the rotation angles on the two axes. By changing the position of the opening, the relationship between the measurement portion and the directions of the mirrors can be obtained. The relationship is stored in a computer or the like. In actual measurement, the directions of the mirrors are controlled according to this relationship.

Mapping measurement using the mapping-measurement apparatus of the present embodiment will be described next.

Figure 5:
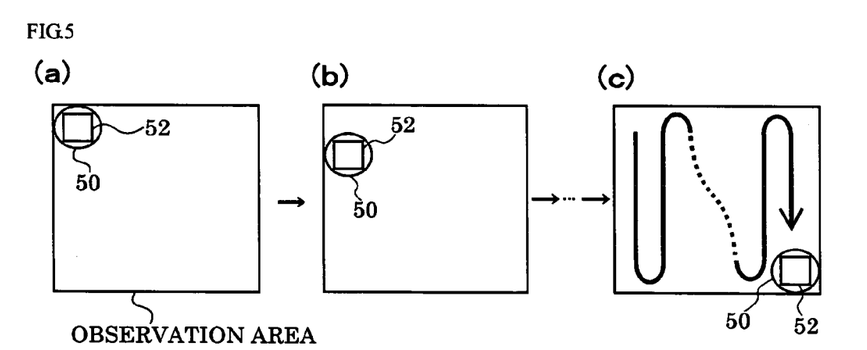
FIG. 5 is an explanatory drawing of mapping measurement.

FIG. 5 is an explanatory view showing mapping measurement. It is assumed here that a single-element detector is used as the photodetector. In FIG. 5, the circular part is an illuminated portion (with a reference numeral 50) illuminated with measurement light, and the square part is a measurement portion (with a reference numeral 52) at which measurement is to be performed by the photodetector. As shown in FIG. 5((*a*) to (*c*)), to perform measurement over the entire observation area, the illuminated portion 50 on the observation plane of the sample is changed by the illumination-side scanning mirror, and the measurement portion 52 is also changed accordingly by the detection-side scanning mirror. Mapping measurement is thus performed at the observation area of the sample.

Since the measurement portion can be changed with the detection-side scanning mirror, mapping measurement is performed without moving the sample itself. In addition, because the measurement portion is efficiently illuminated with measurement light by using the illumination-side scanning mirror, precise measurement is achieved. Further, even if the optical axis of the apparatus is shifted, fine adjustment can be performed just by adjusting the scanning mirrors.

The foregoing description indicates a basic case of mapping measurement using the apparatus according to the present invention. Another case will be described next. In the foregoing description, the illumination portion is changed sequentially. Mapping measurement may be performed with a sufficiently large illumination area of measurement light in which the measurement portion is changed. The size of the illumination area can be adjusted by adjusting the magnification of the objective mirror that collects light coming from the sample or by adjusting the diameter of the light beam emitted from the light illumination unit.

Figure 6:
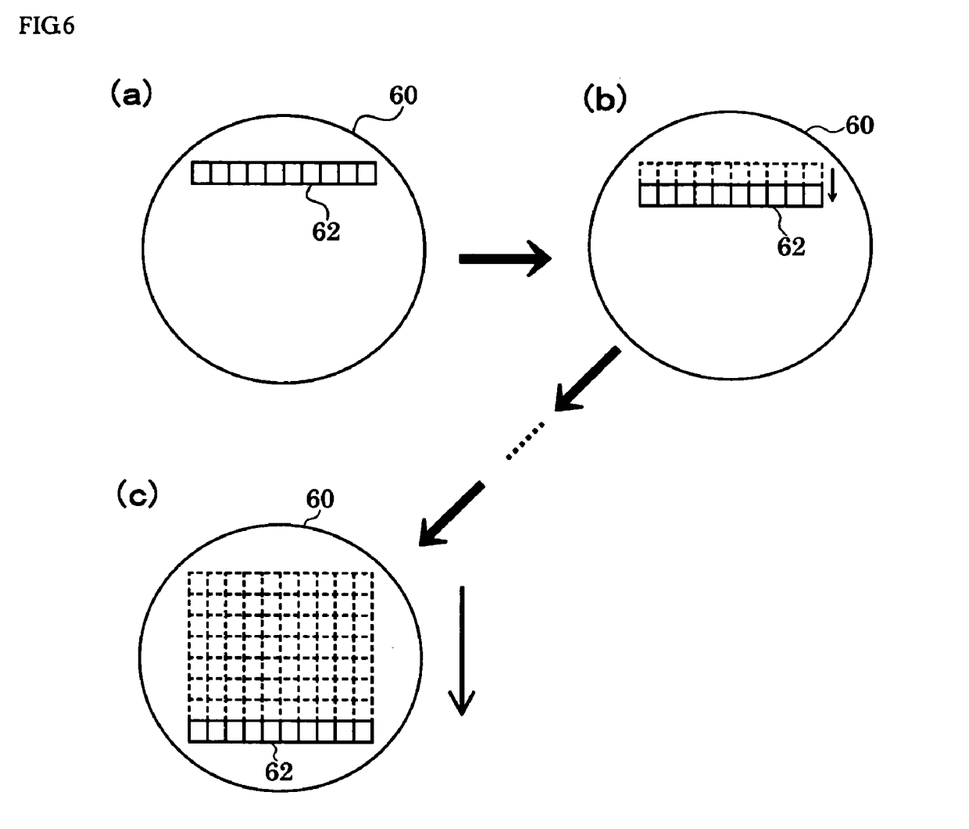
FIG. 6 is an explanatory drawing of mapping measurement.

FIG. 6 shows this case. It is assumed here that a one-dimensional multi-element detector in which light receiving elements are arranged in a row is used as the photodetector. The diameter of the emitted light beam is made sufficiently large to illuminate an area on the surface of the sample where mapping measurement is to be performed. When the illumination area is fixed in this way, the illumination-side scanning mirror is not necessarily required. In FIG. 6, the circular part indicates an illumination portion (with a reference numeral 60). As shown in FIG. 6((*a*) to (*c*)), the measurement portion (with a reference numeral 62) is changed one after another by changing the direction of the detection-side scanning mirror to perform measurement. In (*a*) of FIG. 6, each small square in the measurement portion 62 corresponds to each light receiving element of the one-dimensional multi-element detector. With the use of the function of the detector itself, mapping measurement is performed all at once in the direction in which the light receiving elements are arranged. In (*b*) and (*c*) of FIG. 6, dotted parts indicate areas where measurement has already been completed. As shown in (*c*) of FIG. 6, mapping measurement is performed over the entire illumination area by moving the detection portion in one direction. When a one-dimensional multi-element detector is used, the opening of the aperture should have a slit shape corresponding to the light receiving section of the detector.

Such multi-element detectors can perform measurement at higher speed than detectors having a single light-receiving element, as in FIG. 5.

Figure 7:
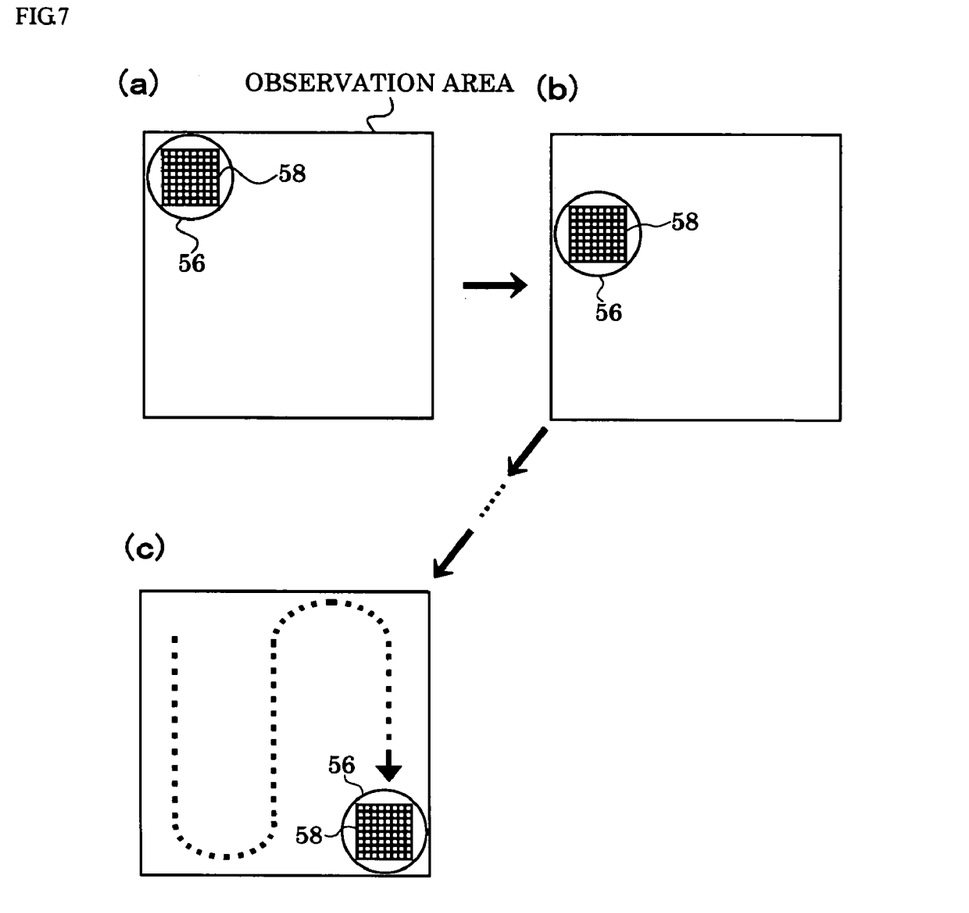
FIG. 7 is an explanatory drawing of mapping measurement.

Even with a multi-element detector, the illumination portion may be changed sequentially to perform mapping measurement, as shown in FIG. 5. A case in which a two-dimensional multi-element detector is used will be described next by referring to FIG. 7.

The size of the illumination portion (with a reference numeral 56) is adjusted so as to cover the measurement portion (with a reference numeral 58) of the detector. Mapping measurement is performed in the illumination portion 56 by a two-dimensional multi-element detector. The illumination portion 56 and the measurement portion 58 are changed in position synchronously, as shown in (*a*) to (*c*) of FIG. 7, to perform mapping measurement. In this way, measurement is performed at high speed using a multi-element detector. In addition, when a scanning mirror is also used, mapping measurement can be applied to a larger area.

Figure 8:
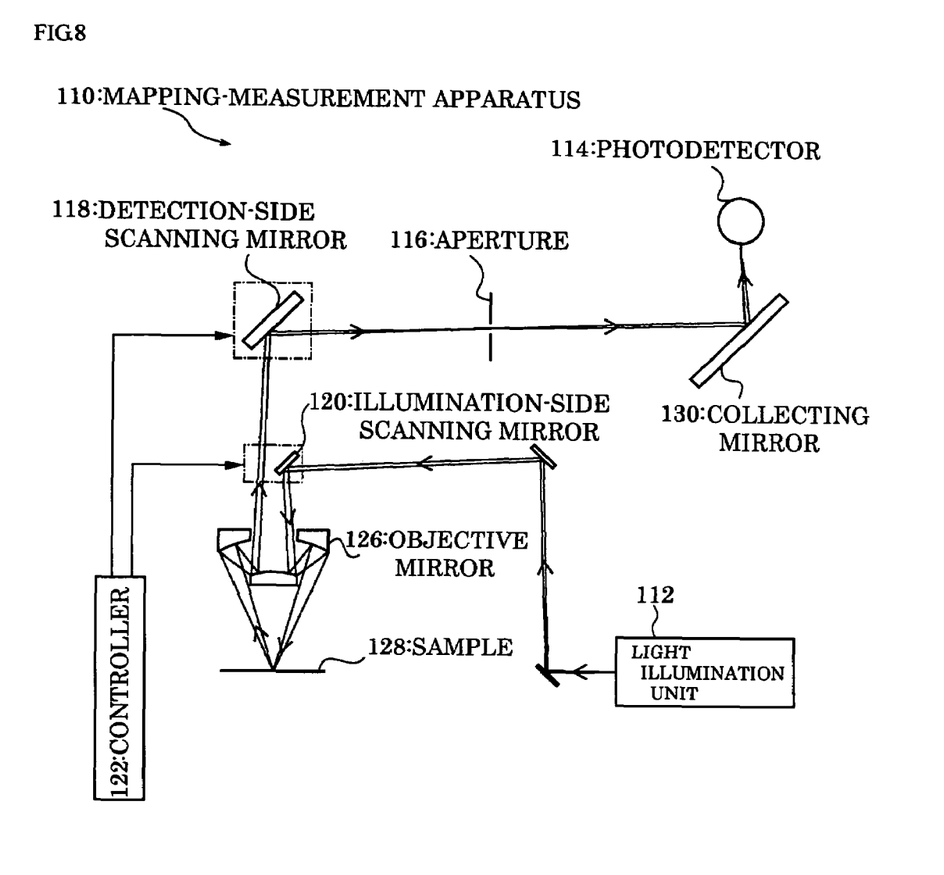
FIG. 8 is an outline structural view of a mapping-measurement apparatus in measuring reflected light.

FIG. 8 is a view showing an optical path when reflected light is measured. FIG. 8 is similar to FIG. 1 in structure. The same sections as those shown in FIG. 1 have the corresponding numerals used in FIG. 1 plus 100, and a description thereof is omitted.

In this case, an illumination-side scanning mirror 120 is disposed at the same side of a sample 128 as a detection-side scanning mirror 118. Light emitted from a light illumination unit 112 is reflected by the illumination-side scanning mirror 120 and sent to an objective mirror 126. The objective mirror 126 focuses light at a specific minute portion of the sample 128. Light reflected by the sample 128 is collected by the objective mirror 126 and sent to the detection-side scanning mirror 118. Then, the light reflected by the sample is directed from the detection-side scanning mirror 118 toward the aperture 116. Only the light corresponding to the measurement portion is selected and detected by a photodetector 114.

Since the illumination-side scanning mirror 120 is disposed close to the optical path between the objective mirror 126 and the detection-side scanning mirror 118, it is necessary to make sure that the illumination-side scanning mirror 120 does not block the optical path. The other sections are almost the same as those described in the transmission measurement shown in FIG. 1.

In the foregoing embodiments, infrared spectrum measurements are described. However, measurement can be performed using light having other wavelengths.

As described above, according to a mapping apparatus of the present invention, mapping measurement is performed by using scanning mirrors without moving a sample Since a mechanism for driving a stage is not necessary, mapping measurement is implemented with a simple apparatus structure.

What is claimed is:

1. A mapping-measurement apparatus for applying mapping measurement to a predetermined area on a surface of a sample, comprising:
   a light illumination unit for illuminating the sample with light;
   a photodetector for detecting, through an aperture, reflection light or transmission light coming from the sample;
   an illumination-side scanning mirror for directing light emitted by the light illumination unit to the sample, wherein the illumination-side scanning mirror is structured such that the direction of a reflection plane thereof can be changed, and wherein the illumination-side scanning mirror has two independent rotational axes,
   a detection-side scanning mirror provided in the optical path from the sample to the aperture, wherein the detection-side scanning mirror is structured such that the direction of a reflection plane thereof may be changed and, wherein the detection-side scanning mirror has two independent rotational axes,
   a controller for controlling the rotation on the rotational axes of at least one of the detection-side scanning mirror or the illumination-side scanning mirror,
   wherein the aperture restricts light to be detected by the photodetector only to light coming from a given measurement portion only on the surface of the sample, and
   wherein the direction of the reflection plane of the detection-side scanning mirror is changed with respect to the incident direction of the reflection light or the transmission light coming from the sample to change the measurement portion on the surface of the sample where measurement is performed by the photodetector, to apply mapping measurement to the predetermined area of the sample.

2. The mapping-measurement apparatus according to claim 1, further comprising an objective mirror disposed in the optical path between the illumination-side scanning mirror and the sample, for focusing the light emitted by the light illumination unit on a specific minute portion on the surface of the sample.

3. The mapping-measurement apparatus according to claim 1, further comprising an objective mirror disposed in the optical path between the detection-side scanning mirror and the sample, for focusing the light emitted by the light illumination unit on a specific minute portion on the surface of the sample.

4. A mapping-measurement apparatus according to claim 1, wherein the photodetector is a single-element detector.

5. A mapping-measurement apparatus according to claim 1, wherein the photodetector is a multi-element detector.

6. A mapping-measurement apparatus as set forth in claim 1 wherein said controller controls the rotation of both said detection-side scanning mirror and said illumination-side scanning mirror.

* * * * *